(12) United States Patent
Juckem et al.

(10) Patent No.: US 9,290,779 B1
(45) Date of Patent: Mar. 22, 2016

(54) TRANSFECTION COMPOSITIONS USING AMPHIPATHIC COMPOUNDS

(71) Applicant: Mirus Bio LLC, Madison, WI (US)

(72) Inventors: Laura Juckem, Madison, WI (US);
Karen Neder, Madison, WI (US);
James Hagstrom, Middleton, WI (US);
Jon Wolff, Madison, WI (US)

(*) Notice: Subject to any disclaimer, the term of this patent is extended or adjusted under 35 U.S.C. 154(b) by 0 days.

(21) Appl. No.: 14/304,957

(22) Filed: Jun. 15, 2014

Related U.S. Application Data (63) Continuation-in-part of application No. 13/364,645, filed on Feb. 2, 2012, now abandoned.

(51) Int. Cl.
| | |
|---|---|
| *A61K 9/00* | (2006.01) |
| *A61K 48/00* | (2006.01) |
| *C12N 15/11* | (2006.01) |
| *C12N 15/87* | (2006.01) |
| *A61K 47/22* | (2006.01) |
| *A61K 47/32* | (2006.01) |

(52) U.S. Cl.
CPC .............. *C12N 15/87* (2013.01); *A61K 47/22* (2013.01); *A61K 47/32* (2013.01)

(58) Field of Classification Search
None
See application file for complete search history.

(56) References Cited

U.S. PATENT DOCUMENTS

| | | | | |
|---|---|---|---|---|
| 5,912,239 | A  * | 6/1999 | Siegel et al. | 514/182 |
| 7,101,995 | B2 * | 9/2006 | Lewis et al. | 536/55 |
| 2007/0110810 | A1* | 5/2007 | Smith | 424/486 |
| 2008/0187570 | A1* | 8/2008 | Jansen et al. | 424/423 |

OTHER PUBLICATIONS

Midoux et al. (Chemical vectors for gene delivery: a current review on polymers, peptides and lipids containing histidine or imidazole as nucleic acids carriers, British Journal of Pharmacology (2009), 157, 166-178).*

* cited by examiner

*Primary Examiner* — Ernst V Arnold
*Assistant Examiner* — Jianfeng Song
(74) *Attorney, Agent, or Firm* — Mark K Johnson (57) ABSTRACT

A low toxicity, highly efficient transfection composition is described with an amphipathic compound containing at least one imidazole. The composition may be used in the process of transfecting nucleic acids into an animal cell.

6 Claims, 6 Drawing Sheets

TRANSFECTION COMPOSITIONS USING AMPHIPATHIC COMPOUNDS

This is a continuation-in-part claiming the benefit of non-provisional application Ser. No. 13/364,645 filed on Feb. 2, 2012 which is hereby incorporated by reference.

FIELD OF THE INVENTION

The field of the present invention is a composition comprising nucleic acids, amphipathic compounds and polycations and the use of such compositions for delivering the nucleic acids to an animal cell.

BACKGROUND

Transfection is any method for introducing foreign molecules into a cell (e.g., a bacterial, yeast, fungal, plant, insect, or animal cell, particularly a vertebrate or mammalian cell). The cell may be in an animal. Lipofection, DEAE-dextran-mediated transfection, microinjection, protoplast fusion, calcium phosphate precipitation, viral or retroviral delivery, electroporation, and biolistic transformation are just a few of the transfection methods known to those skilled in the art. The nucleic acid may be, for example, naked RNA or DNA. Other RNA and/or DNA delivery agents may comprise a cationic lipid and liposome.

The efficient delivery of biologically active compounds to the intracellular space of cells has been accomplished by the use of a wide variety of vesicles. One particular type of vesicle, liposomes, is one of the most developed types of vesicles for drug delivery. Liposomes, which have been under development since the 1970's, are microscopic vesicles that comprise amphipathic molecules which contain both hydrophobic and hydrophilic regions. Liposomes can be formed from one type of amphipathic molecule or several different amphipathic molecules. Several methods have been developed to complex biologically active compounds with liposomes. In particular, polynucleotides complexed with liposomes have been delivered to mammalian cells. After publication of DOTMA (N-[1-(2,3-dioleyloxy)propyl]-N,N,N-trimethylammonium chloride), a number of cationic lipids have been synthesized for this purpose. Essentially all the cationic lipids are amphipathic compounds that contain a hydrophobic domain, a spacer, and positively-charged amine(s). The cationic lipids are sometimes mixed with a fusogenic lipid such as DOPE (dioleoyl phosphatidyl ethanolamine) to form liposomes. The cationic liposomes are then mixed with plasmid DNA and the binary complex of the DNA and liposomes are applied to cells in a tissue culture dish or injected in vivo. The ease of mixing the plasmid DNA with the cationic liposome formulation, the ability of the cationic lipids to complex with DNA and the relative high levels of transfection efficiency has led to increasing use of these formulations. However, these cationic lipid formulations have a common deficiency in that they are typically toxic to the cells in culture and in vivo. More recently lipids have been used in association with other DNA-binding compounds to facilitate cell transfection.

The present invention provides new amphipathic compounds, and methods of preparation, to be used to prepare novel complexes of biologically active polyions for delivery to animal cells in vitro and in vivo. The complexes facilitate high efficiency transfer of the polyion from outside the cell to the inside a cell with low toxicity.

SUMMARY AND DETAILED DESCRIPTION

The present invention provides nucleic acid transfer into animal cells using a ternary complex comprising nucleic acid, an amphipathic compound, and a polycation. A novel amphipathic compound and method of preparation thereof, is described.

In a preferred embodiment, compositions comprising nucleic acids, amphipathic compounds and polycations, and processes using such compositions to deliver a nucleic acid to an animal cell in vivo or in vitro for the purposes of altering expression of a gene in the cell are described.

In a preferred embodiment, compositions and compounds are described that facilitate delivery of nucleic acid to an animal cell in vitro and in vivo. The nucleic acid comprises a double stranded structure having a nucleotide sequence substantially identical to an expressed target gene within the cell. Further, the use of a polycation and a novel amphipathic compound together significantly increased nucleic acid transfer efficiency. The nucleic acid then alters expression of a selected gene.

In a preferred embodiment, the polycation is a polymer such as poly-L-lysine, polyethylenimine (PEI), polysilazane, polydihydroimidazolinium, polyallylamine and the like. A preferred cationic polymer is ethoxylated polyethylenimine (ePEI).

Figure 4:
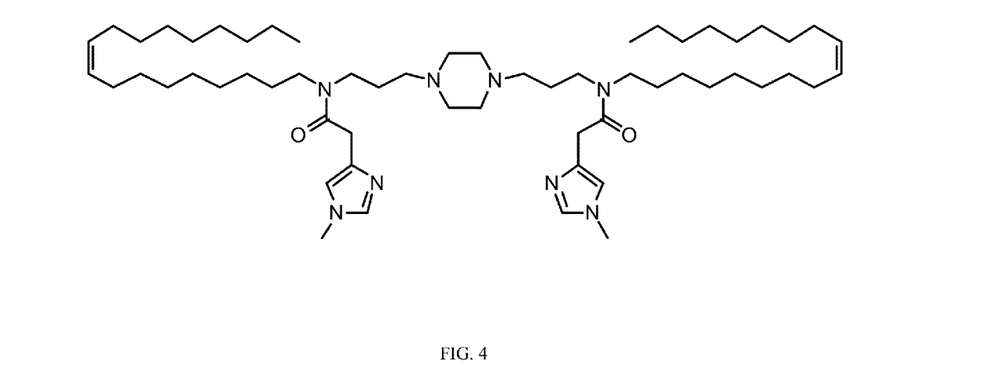
FIG. 4 illustrates the structure of the compound Bis-(Methyllmidazole)ODAP (Bis-Me-Im-ODAP).

In a preferred embodiment, ePEI or a similar polymer is used as the polycation and an amphipathic compound such as Bis-Glycine-ODAP, Bis-Pyridyl-ODAP or Bis-Im-ODAP. A preferred amphipathic compound is Bis-Me-Im-ODAP (see FIG. 4).

In a preferred embodiment, the cell can be an animal cell that is maintained in tissue culture such as cell lines that are immortalized or transformed. These include a number of cell lines that can be obtained from American Type Culture Collection (Bethesda) such as, but not limited to: 3T3 (mouse fibroblast) cells, Rat 1 (rat fibroblast) cells, CHO (Chinese hamster ovary) cells, CV-1 (monkey kidney) cells, COS (monkey kidney) cells, 293 (human embryonic kidney) cells, HeLa (human cervical carcinoma) cells, HepG2 (human hepatocytes) cells, Sf9 (insect ovarian epithelial) cells and the like.

In another preferred embodiment, the cell can be a primary or secondary cell which means that the cell has been maintained in culture for a relatively short time after being obtained from an animal. These include, but are not limited to primary liver cells and primary muscle cells and the like. The cells within the tissue are separated by mincing and digestion with enzymes such as trypsin or collagenases which destroy the extracellular matrix. Tissues consist of several different cell types and purification methods such as gradient centrifugation or antibody sorting can be used to obtain purified amounts of the preferred cell type. For example, primary myoblasts are separated from contaminating fibroblasts using Percoll (Sigma) gradient centrifugation. In another preferred embodiment, the cell can be an animal cell that is within the tissue in situ or in vivo meaning that the cell has not been removed from the tissue or the animal. In a preferred embodiment a process is described for delivering an nucleic acid into an animal cell for the purposes of altering expression of a gene comprising forming a complex with an amphipathic compound, an effective amount of a polycation and an nucleic acid in solution, and associating the cell with the ternary complex.

A preferred amphipathic compound is a Bis-Me-Im-ODAP compound.

A preferred polycation is ePEI.

In contrast to the use of cationic liposomes used for gene transfer, the novel amphipathic compound described above does not efficiently mediate the transfer of genes into cells when used alone. However, the use of polycations with this novel amphipathic compound enables the efficient gene transfer into a variety of animal cells with minimal cellular toxicity. The combination of polycation and amphipathic compounds enhances the efficiency of nucleic acid delivery.

In a preferred embodiment, the present invention provides a process for delivering a nucleic acid to an animal cell comprising; preparing a ternary complex comprising mixing a compound of Bis-Me-Im-ODAP with a nucleic acid and a polycation in a solution, associating the complex with an animal cell, and delivering the nucleic acid to the interior of the cell. The nucleic acid then alters expression of a gene in the cell. The amphipathic compound may be mixed with the polycation prior to addition of the nucleic acid, at the same time as the nucleic acid, or after the nucleic acid.

In a preferred embodiment, we describe a complex for altering nucleic acid expression in a cell. The complex comprises mixing a nucleic acid and a compound or compounds to form the complex wherein the zeta potential of the complex is less negative than the zeta potential of the nucleic acid alone.

In a preferred embodiment, the polycation, the nucleic acid, or the amphipathic compound may be modified by attachment of a functional group. The functional group can be, but is not limited to, a targeting signal or a label or other group that facilitates delivery of the nucleic acid. The group may be attached to one or more of the components prior to complex formation. Alternatively, the group(s) may be attached to the complex after formation of the complex. In a preferred embodiment the compound, compositions, and processes for delivery of a nucleic acid to an animal cell can be used wherein the cell is located in vitro, ex vivo, in situ, or in vivo.

The Bis-Me-Im-ODAP compound is considered amphipathic because the molecule contains a portion that is hydrophilic while another portion is hydrophobic. Hydrophobic groups indicate in qualitative terms that the chemical moiety is water-avoiding. Typically, hydrophobic groups indicate in qualitative terms that the chemical moiety is water-avoiding. Hydrocarbons are hydrophobic groups. Hydrophilic groups indicate in qualitative terms that the chemical moiety is water-preferring. Typically, such chemical groups are water soluble, and are hydrogen bond donors or acceptors with water. Examples of hydrophilic groups include compounds with the following chemical moieties; carbohydrates, polyoxyethylene, peptides, oligonucleotides, and groups containing amines, amides, alkoxyamides, carboxylic acids, sulfurs, or hydroxyls.

Polymers

A polymer is a molecule built up by repetitive bonding together of smaller units called monomers. In this application the term polymer includes both oligomers which have two to about 80 monomers and polymers having more than 80 monomers. The polymer can be linear, branched network, star, comb, or ladder types of polymer. The polymer can be a homopolymer in which a single monomer is used or can be copolymer in which two or more monomers are used. Types of copolymers include alternating, random, block and graft. The main chain of a polymer is composed of the atoms whose bonds are required for propagation of polymer length. The side chain of a polymer is composed of the atoms whose bonds are not required for propagation of polymer length. To those skilled in the art of polymerization, there are several categories of polymerization processes that can be utilized in the described process. The polymerization can be chain or step. This classification description is more often used that the previous terminology of addition and condensation polymer. "Most step-reaction polymerizations are condensation processes and most chain-reaction polymerizations are addition processes" (M. P. Stevens Polymer Chemistry: An Introduction New York Oxford University Press 1990). Template polymerization can be used to form polymers from daughter polymers. Step Polymerization: In step polymerization, the polymerization occurs in a stepwise fashion. Polymer growth occurs by reaction between monomers, oligomers and polymers. No initiator is needed since there is the same reaction throughout and there is no termination step so that the end groups are still reactive. The polymerization rate decreases as the functional groups are consumed. Typically, step polymerization is done either of two different ways. One way, the monomer has both reactive functional groups (A and B) in the same molecule so that A-B yields -[A-B]- Or the other approach is to have two difunctional monomers. A-A+B-B yields -[A-A-B-B]

Generally, these reactions can involve acylation or alkylation. Acylation is defined as the introduction of an acyl group (—COR) onto a molecule. Alkylation is defined as the introduction of an alkyl group onto a molecule. If functional group A is an amine then B can be (but not restricted to) an isothiocyanate, 5 isocyanate, acyl azide, N-hydroxysuccinimide, sulfonyl chloride, aldehyde (including formaldehyde and glutaraldehyde), ketone, epoxide, carbonate, imidoester, carboxylate, oralkylphosphate, arylhalides (difluoro-dinitrobenzene), anhydrides or acid halides, pnitrophenylesters, o-nitrophenyl pentachlorophenyl esters, or pentafluorophenyl esters. In other terms when function A is an amine then function B can be acylating or alkylating agent or amination. If functional group A is a thiol, sulfhydryl, then function B can be (but not restricted to) aniodoacetyl derivative, maleimide, aziridine derivative, acryloyl derivative, fluorobenzene derivatives, or disulfide derivative (such as a pyridyl disulfide or 5-thio-2-nitrobenzoic acid {TNB} derivatives). If functional group A is carboxylate then function B can be (but not restricted to) a diazoacetate or an amine in which a carbodiimide is used. Other additives may be utilized such as carbonyldiimidazole, dimethylaminopyridine, N-hydroxysuccinimide or alcohol using carbodiimide and dimethylaminopyridine.

If functional group A is a hydroxyl then function B can be (but not restricted to) an epoxide, oxirane, or an amine in which carbonyldiimidazole or N,N'-disuccinimidyl carbonate, or N-hydroxysuccinimidyl chloroformate or other chloroformates are used. If functional group A is an aldehyde or ketone then function B can be (but not restricted to) an hydrazine, hydrazide derivative, amine (to form a imine or iminium that may or may not be reduced by reducing agents such as $NaCNBH_3$) or hydroxyl compound to form a ketal or acetal.

Yet another approach is to have one difunctional monomer so that A-A plus another agent yields -[A-A]-. If function A is a thiol, sulfhydryl, group then it can be converted to disulfide bonds by oxidizing agents such as iodine ($I_2$) or $NaIO_4$ (sodium periodate), or oxygen ($O_2$). Function A can also be an amine that is converted to a thiol, sulfhydryl, group by reaction with 2-iminothiolate (Traut's reagent) which then undergoes oxidation and disulfide formation. Disulfide derivatives (such as a pyridyl disulfide or 5-thio-2-nitrobenzoic acid {TNB} derivatives) can also be used to catalyze disulfide bond formation.

Functional group A or B in any of the above examples could also be a photoreactive group such as aryl azides, halogenated aryl azides, diazo, benzophenones, alkynes or diazirinederivatives. Reactions of the amine, hydroxyl, thiol, sulfhydryl, carboxylate groups yield chemical bonds that are described as amide, amidine, disulfide, ethers, esters, enamine, urea, isothiourea, isourea, sulfonamide, carbamate, carbon-nitrogen double bond (imine), alkylamine bond (secondary amine), carbon-nitrogen single bonds in which the carbon contains a hydroxylgroup, thio-ether, diol, hydrazone, diazo, or sulfone. Chain Polymerization: In chain-reaction polymerization growth of the polymer occurs by successive addition of monomer units to limited number of growing chains. The initiation and propagation mechanisms are different and there is usually a chain-terminating step. The polymerization rate remains constant until the monomer is depleted. Monomers containing vinyl, acrylate, methacrylate, acrylamide, methacrylamide groups can undergo chain reaction, which can be radical, anionic, or cationic. Chain polymerization can also be accomplished by cycle or ring opening polymerization. Several different types of free radical initiators could be used that include peroxides, hydroxyperoxides, and azo compounds such as 2,2'-azobis(-amidinopropane) dihydrochloride (AAP). A compound is a material made up of two or more elements.

Types of Monomers:

A wide variety of monomers can be used in the polymerization processes. These include positive charged organic monomers such as amines, imidine, guanidine, imine, hydroxylamine, hydrazine, heterocycles (like imidazole, pyridine, morpholine, pyrimidine, or pyrene). The amines could be pH-sensitive in that the pKa of the amine is within the physiologic range of 4 to 8. Specific amines include spermine, spermidine, N,N'-bis(2-aminoethyl)-1,3-propanediamine (AEPD), and 3,3'-diamino-N,N-25 dimethyldipropylammonium bromide. Monomers can also be hydrophobic, hydrophilic or amphipathic. Monomers can also be intercalating agents such as acridine, thiazole orange, or ethidium bromide. Other components of the monomers and polymers: The polymers have other groups that increase their utility. These groups can be incorporated into monomers prior to polymer formation or attached to the polymer after its formation. These groups include: targeting groups—such groups are used for targeting the polymer-nucleic acid complexes to specific cells or tissues. Examples of such targeting agents include agents that target to the asialoglycoprotein receptor by using asioglycoproteins or galactose residues. Other proteins such as insulin, EOF, or transferrin can be used for targeting.

Protein refers to a molecule made up of 2 or more amino acid residues connected one to another as in a polypeptide. The amino acids may be naturally occurring or synthetic. Peptides that include the ROD sequence can be used to target many cells. Chemical groups that react with thiol, sulfhydryl, or disulfide groups on cells can also be used to target many types of cells. Folate and other vitamins can also be used for targeting. Other targeting groups include molecules that interact with membranes such as fatty acids, cholesterol, dansyl compounds, and amphotericin derivatives. After interaction of the supramolecular complexes with the cell, other targeting groups can be used to increase the delivery of the drug or nucleic acid to certain parts of the cell. For example, agents can be used to disrupt endosomes and a nuclear localizing signal (NLS) can be used to target the nucleus. A variety of ligands have been used to target drugs and genes to cells and to specific cellular receptors. The ligand may seek a target within the cell membrane, on the cell membrane or near a cell. Binding of ligands to receptors typically initiates endocytosis. Ligands could also be used for DNA delivery that bind to receptors that are not endocytosed. For example peptides containing peptide sequence that bind integrin receptor could be used. In addition viral proteins could be used to bind the complex to cells. Lipids and steroids could be used to directly insert a complex into cellular membranes. The polymers can also contain cleavable groups within themselves. When attached to the targeting group, cleavage leads to reduce interaction between the complex and the receptor for the targeting group. Cleavable groups include but are not restricted to disulfide bonds, diols, diazo bonds, ester bonds, sulfone bonds, acetals, ketals, enol ethers, enol esters, enamines and imines.

Polyelectrolyte

A polyelectrolyte, or polyion, is a polymer possessing more than one charge, i.e. the polymer contains groups that have either gained or lost one or more electrons. A polycation is a polyelectrolyte possessing net positive charge, for example poly-L-lysine hydrobromide. The polycation can contain monomer units that are charge positive, charge neutral, or charge negative, however, the net charge of the polymer must be positive. A polycation also can mean a non-polymeric molecule that contains two or more positive charges. A polyanion is a polyelectrolyte containing a net negative charge. The polyanion can contain monomer units that are charge negative, charge neutral, or charge positive, however, the net charge on the polymer must be negative. A polyanion can also mean a non-polymeric molecule that contains two or more negative charges. The term polyelectrolyte includes polycation, polyanion, zwitterionic polymers, and neutral polymers. The term zwitterionic refers to the product (salt) of the reaction between an acidic group and a basic group that are part of the same molecule.

Acrylamides

RNA interference (RNAi) is a phenomenon wherein double-stranded RNA, when present in a cell, inhibits expression of a gene that has an identical or nearly identical sequence. Inhibition is caused by degradation of the messenger RNA (mRNA) transcribed from the target gene. The double-stranded RNA responsible for inducing RNAi is termed interfering RNA. dsRNA introduced into the cytoplasm of a cell is first processed into RNA fragments 21-25 nucleotides long. It has been shown in in vitro studies that these dsRNAs, termed small interfering RNAs (siRNA) are generated at least in part by the RNAse III-like enzyme Dicer. Each siRNA is unwound into two single-stranded (ss) ssRNAs, the passenger strand and the guide strand. The passenger strand is degraded, and the guide strand is incorporated into the RNA-induced silencing complex (RISC). The most studied outcome is post-transcriptional gene silencing, which occurs when the guide strand base pairs with a complementary sequence in a messenger RNA molecule and induces cleavage by Argonaute, the catalytic component of the RISC complex.

RNAi has become a valuable research tool, both in cell culture and in living organisms, because synthetic dsRNA introduced into cells can selectively and robustly induce suppression of specific genes of interest. RNAi may be used for large-scale screens that systematically shut down each gene in the cell, which can help identify the components necessary for a particular cellular process or an event such as cell division. The pathway is also used as a practical tool in biotechnology and medicine. The cationic polyacrylamides described in this specification provide a mechanism to transfect siRNA and other nucleic acids into cells.

The acrylamide repeat units of the polycations described here have one or more amines present on the side chain. The amines can be either primary, secondary, or tertiary, or a combination thereof. The precursor acrylamide monomers containing primary and/or secondary amine side groups are protected with tert-butoxycarbonyl (BOC) protecting moieties. The BOC protected acrylamide monomers can be used to form homopolymers or various types of copolymers with acrylamide and/or acrylate co-monomers. The BOC groups are subsequently removed under acidic conditions post-polymerization to form the required polycations.

The development, synthesis, and characterization of cationic, acrylamide polymers are described. Various acrylamide polymers containing tertiary, secondary, and/or primary amines were synthesized using free radical polymerization. Specifically, reversible-addition fragmentation chain transfer (RAFT) polymerization was used to synthesize polyacrylamides with well defined structures, compositions, and molecular weights (Mw/Mn<1.5). Architectures include, but are not limited to, random/statistical, gradient, block, linear, branched, cross-linked/network, star, and dendritic structures. RAFT has rivaled other controlled free radical polymerization techniques such as atom transfer radical polymerization (ATRP) as one of the most effective ways to synthesize well-defined and novel polymers. The controlled synthesis of RAFT polymers is achieved using conventional radical initiators such as azobisisobutyronitrile (AIBN), and the reversible chain transfer of dithiocarbonyl compounds.

Monomer synthesis: Polymers with an acrylamide or methacrylamide backbone and an alkyl side group (two or more carbons) containing one or more primary, secondary, or tertiary amines. Copolymers in which at least one of the repeat units are a class of acrylamide or methacrylamide with an alkyl side group containing an amine are also described. The copolymers can be a combination of two or more different cationic repeat unit structures, or can be a combination of (meth)acrylamide and (meth)acrylate cationic units. Copolymers can be a combination of (meth)acrylamide cationic units and alkyl (meth)acrylamide units, or can be a combination of (meth)acrylamide cationic units and alkyl (meth)acrylate units.

Figure 1:
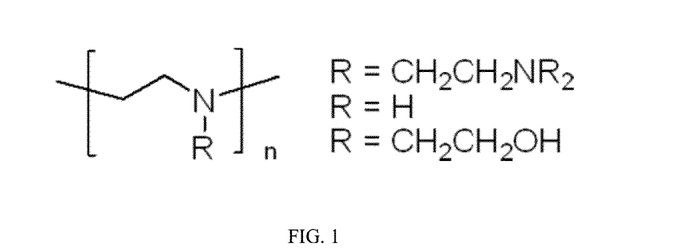
FIG. 1 illustrates the structure of EPEI from the Sigma catalogue (#306185).
Figure 2:
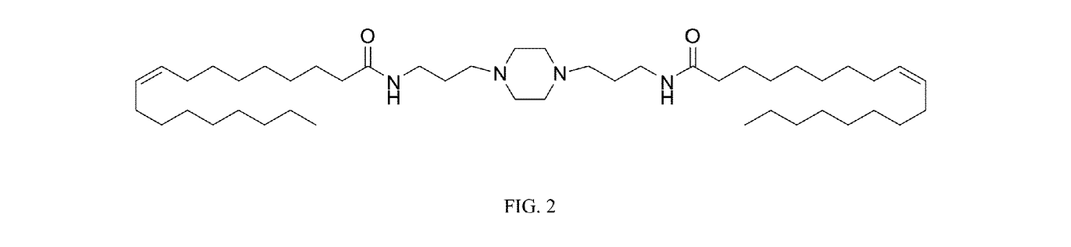
FIG. 2 illustrates the structure of a first intermediate compound.
Figure 3:
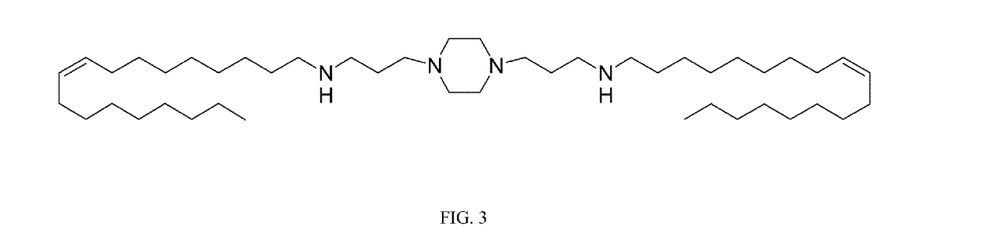
FIG. 3 illustrates the structure of a second intermediate compound.

All acrylamide monomers were synthesized based on the reaction of either acryloyl chloride or methacryloyl chloride with a primary amine containing moiety in the presence of a base (FIG. 1). The synthesis of 1-(N-BOC-piperidyl)-4-acrylamide (14PipAm) is described here as an example:

4-amino-1-boc-piperidine (5.00 g, 0.025 mol) was dissolved in dichloromethane (50 mL) and added to a dry 250 mL 3 neck round bottom flask flushed with nitrogen and equipped with a dropping funnel and stirrer bar. The flask was immersed in an ice bath before acryloyl chloride (2.47 g, 0.0272 mol) in dichloromethane (15 mL) was added to the stirring solution drop-wise via the dropping funnel over a period of 45 min. The solution was stirred overnight and allowed to warm to room temperature. The solution was washed with 10% w/v citric acid solution (20 mL), 10% potassium carbonate solution (20 mL), saturated sodium bicarbonate solution (20 mL), and brine (20 mL). The organic layer was then dried over sodium sulfate and passed through a basic alumina plug. The solvent was then removed by rotor evaporation at room temperature. The oil product was dissolved in dichloromethane (10 mL) and precipitate three times into hexane. If necessary, a silica column is also used to purify the monomer. Yield=4.0 g (63%). $^1$H NMR, (CDCl$_3$) ppm: 1.32 (2H), 1.45 (9H), 1.95 (2H), 2.87 (2H), 4.03 (3H), 5.52 (1H), 5.66 (1H), 6.10 (1H), 6.30 (1H).

Polymer synthesis: The monomers described were polymerized using RAFT in order to synthesize polymers of well-defined molecular weights, compositions, and architectures. The synthesis of poly(1-piperidyl)-4-acrylamide) (P14PipAm) is given as an example.

1-(N-BOC-piperidyl)-4-acrylamide (0.200 g, 0.787 mmol), 4-cyano-4(phenylcarbonothioylthio)pentanoic acid (CPCPA, 1.12 mg, 0.00401 mmol), AIBN (0.098 mg, 0.00060 mmol), and butyl acetate (1.00 mL) were added to a 20 mL glass vial with stirrer bar. The vial was sealed with a rubber cap and the solution bubbled with nitrogen using a long syringe with a second syringe as the outlet for 1 h. The syringes were removed and the vial heated to 80° C. for 15 h using an oil bath. The solution was allowed to cool to room temperature and precipitated into hexane. The product was re-dissolved in dichloromethane and precipitated into hexane dried under reduced pressure for several hours. Yield=0.181 mg (90%). $^1$H NMR, (CDCl$_3$) ppm: 1.4 (9H), 1.8 (3H), 2.2 (2H), 2.8 (2H), 3.8 (2H), 4.0 (3H).

The BOC protected polyaminoacrylamides were deprotected post-polymerization to yield primary and secondary amines in the polymer side groups. The deprotection of P14PipAm-BOC is described as an example.

P14PipAm-BOC (0.150 g) was dissolved in a 2 N HCl solution of acetic acidic (4 mL) and stirred for 1 h. Water (15 mL) was added to the solution, which was then dialyzed against salt water and then deionized water over a period of 48 h. The dialyzed solution was then frozen and lyophilized to dryness (Yield=0.080 g).

Steric Stabilizer

A steric stabilizer is a long chain hydrophilic group that prevents aggregation of final polymer by sterically hindering particle to particle electrostatic interactions. Examples include: alkyl groups, PEG chains, polysaccharides, alkyl amines. Electrostatic interactions are the non-covalent association of two or more substances due to attractive forces between positive and negative charges.

Buffers

Buffers are made from a weak acid or weak base and their salts. Buffer solutions resist changes in pH when additional acid or base is added to the solution.

Biochemical Reactions

Biological, chemical, or biochemical reactions involve the formation or cleavage of ionic and/or covalent bonds.

Reactive

A compound is reactive if it is capable of forming either an ionic or a covalent bond with another compound. The portions of reactive compounds that are capable of forming covalent bonds are referred to as reactive functional groups.

Steroid

A steroid derivative means a sterol, a sterol in which the hydroxyl moiety has been modified (for example, acylated), or a steroid hormone, or an analog thereof. The modification can include spacer groups, linkers, or reactive groups.

Sterics

Steric hindrance, or sterics, is the prevention or retardation of a chemical reaction because of neighboring groups on the same molecule.

EXAMPLES

Example 1

EPEI

Sigma catalogue #306185 (see FIG. 1)

Example 2

Intermediate lipid compound (MC798)

A solution of 49.63 g (164.9 mmol) of oleoyl chloride in 220 mL of $CHCl_3$ was added dropwise over 2 hr to a solution of 16.52 g (82.46 mmol) of N,N'-bis-(3-aminopropyl)piperazine and 28.727 mL (164.9 mmol) of diisopropylethylamine (DIEA) in 200 mL of $CHCl_3$. The reaction mixture was stirred overnight at room temperature. The reaction mixture was diluted with 400 mL $CHCl_3$, washed with saturated $Na_2CO_3$ (3×200 mL), washed with saturated NaCl (250 mL), dried with $MgSO_4$, and the solvent was removed under vacuum. The residue was recrystallized to constant melting point from acetonitrile (2 L), to yield 51.5 g (86%) of MC798 as a white powder: m.p. 81.8-82.6° C.; $R_f$=0.53 ($CHCl_3$/MeOH=9:1) ($KMnO_4$); $^1H$ NMR (400 MHz, $CDCl_3$, TMS) 6.85 (br t, 2H), 5.4-5.3 (m, 4H), 3.34 (q, J=6.0 Hz, 4H), 2.7-2.4 (v br m, 8H), 2.46 (t, J=6.2 Hz, 4H), 2.2-2.1 (m, 4H), 2.1-2.0 (m, 8H), 1.7-1.6 (m, 8H), 1.4-1.2 (m, 40H), 0.88 (t, J=6.8 Hz, 6H); MS (ESI) m/z 729.9 ($M^+$).

Example 3

Imidazole PAA (Im-PAA)

Polyallylamine (MW 15,000) was dissolved in 25 mM MES (pH 6.5) at about 50 mg/mL. To this solution was added 0.5-1 molar equivalents (relative to amine content of polyallylamine) of 4-imidazoleacetic acid. N-Hydroxysuccinimide (NHS) (1.3 equivalents to imidazoleacetic acid) was dissolved in 25 mM MES (pH 6.5) at 4 mg/mL. To the polyallylamine/imidazoleacetic acid solution was added N-(3-dimethylaminopropyl)-N'-ethylcarbodiimide (EDC) (2 equivalents to imidazoleacetic acid). Once the EDC was dissolved, the NHS solution was added to the reaction mixture. The reaction mixture was stirred at room temperature for 24 hr. The reaction mixture was then transferred to dialysis tubing (MWCO 3500) and dialyzed against NaCl (2 g per 100 mL of water) for 24 hr, then against HCl (pH 2-3) for 24 hr, then against water for 24 hr. Removal from the tubing and lyophilization afforded the polymer as a white powder.

Example 4

Second Intermediate Lipid (ODAP)

To a stirred suspension of 1.561 g (41.13 mmol) of lithium aluminum hydride in 200 mL of tetrahydrofuran was added dropwise a solution of 10.00 g (13.71 mmol) of MC798 in 200 mL of tetrahydrofuran. When the addition was complete, the reaction mixture was refluxed under nitrogen for 19 hr. The reaction mixture was cooled (cold water bath), and excess hydride was decomposed by careful dropwise addition of 1.561 mL of water, then 1.561 mL of 15% NaOH, and then 4.683 mL of water. The mixture was stirred for 45 min, filtered, and the precipitate was washed with tetrahydrofuran. The filtrate was diluted with $CHCl_3$ (600 mL), washed with water (2×200 mL), washed with saturated NaCl (250 mL), dried with $MgSO_4$, and evaporated. Column chromatography on silical gel with $CHCl_3$/MeOH/$NH_4OH$=90:10:1 afforded 7.58 g (78%) of ODAP as a waxy solid: $^1H$ NMR (400 MHz, $CDCl_3$, TMS) 5.4-5.3 (m, 4H), 2.64 (t, J=6.8 Hz, 4H), 2.58 (t, J=7.3 Hz, 4H), 2.6-2.3 (m, 8H), 2.39 (t, J=7.3 Hz, 4H), 2.1-2.0 (m, 8H), 1.7-1.6 (m, 4H), 1.5-1.4 (m, 4H), 1.4-1.2 (m, 44H), 0.88 (t, J=6.8 Hz, 6H); MS (ESI) m/z 701.5 ($M^+$), 351.3 ($M^{+2}$).

Example 4

Bis-Imidazole-ODAP

To a suspension of 1.817 g (11.18 mmol) of 4-imidazoleacetic acid hydrochloride in 120 mL of $CHCl_3$ was added 8.00 mL (45.9 mmol) of DIEA. Then 4.239 g (11.18 mmol) of HBTU were added. After stirring for 15 min, a solution of 3.267 g (4.658 mmol) of ODAP in 80 mL of $CHCl_3$ was added to the reaction mixture. After refluxing for 6.5 hr, the reaction mixture was rotovapped to remove $CHCl_3$, followed by distillation on Kugelrohr apparatus to remove DIEA. The residue was dissolved in $CHCl_3$ (700 mL), washed with saturated $Na_2CO_3$ (3×200 mL), washed with saturated NaCl (250 mL), dried with $MgSO_4$, and evaporated. Column chromatography on silica gel with $CHCl_3$/MeOH/$NH_4OH$=85:15:0.5 then 85:15:1, afforded 3.455 g (81%) of Bis-Imidazole-ODAP as a light orange oil: $R_f$=0.45 ($CHCl_3$/MeOH/$NH_4OH$=85:15:1), 0.35 ($CHCl_3$/MeOH/$NH_4OH$=85:15:0.5); $^1H$ NMR (400 MHz, $CDCl_3$, TMS) 7.56 (m, 2H), 6.90 (m, 2H), 5.4-5.3 (m, 4H), 3.81 (d, 2H), 3.69 (d, 2H), 3.4-3.3 (m, 8H), 2.5-2.2 (m, 12H), 2.1-2.0 (m, 8H), 1.8-1.7 (m, 4H), 1.6-1.5 (m, 4H), 1.4-1.2 (m, 44H), 0.88 (t, J=7.0 Hz, 6H); MS (ESI) m/z 918.0 ($M^+$), 459.6 ($M^{+2}$).

Example 5

Bis-Me-Im-ODAP

To a suspension of 45.1 mg (2.554×$10^{-4}$ mol) of 1-methyl-4-imidazoleacetic acid hydrochloride in 2 mL of $CHCl_3$ was added 185 L (1.062 mmol) of DIEA. Then 96.7 mg (2.550×$10^{-4}$ mol) of HBTU were added. After stirring for 15 min, a solution of 74.6 mg (1.064×$10^{-4}$ mol) of ODAP in 1 mL of $CHCl_3$ was added to the reaction mixture. After refluxing for 6 hr, the reaction mixture was diluted with $CHCl_3$ (50 mL), washed with saturated $Na_2CO_3$ (2×25 mL), dried with $MgSO_4$, and evaporated. Column chromatography on silica gel with $CHCl_3$/MeOH/$NH_4OH$=85:15:1 afforded 93.5 mg (92%) of bis-Me-Im-ODAP as an orange oil: $R_f$=0.58 ($CHCl_3$/MeOH/$NH_4OH$=85:15:1) ($I_2$ or $KMnO_4$); $^1H$ NMR (400 MHz, $CDCl_3$, TMS) 7.31 (s, 2H), 6.86 (s, 2H), 5.4-5.3 (m, 4H), 3.68 (s, 2H), 3.64 (s, 2H), 3.63 (s, 6H), 3.5-3.4 (m, 2H), 3.4-3.3 (m, 6H), 2.6-2.3 (v br, 8H), 2.4-2.3 (m, 4H), 2.1-2.0 (m, 8H), 1.8-1.7 (m, 4H), 1.6-1.5 (m, 4H), 1.4-1.2 (m, 44H), 0.88 (t, J=6.8 Hz, 6H); MS (ESI) m/z 946.0 ($M^+$), 473.6 ($M^{2+}$).

Example 6

Bis-Glycine-ODAP

To a solution of 90.8 mg (1.294×$10^{-4}$ mol) of ODAP in 4 mL of THF was added 47.4 L (2.721×$10^{-4}$ mol) of DIEA, followed by 74.1 mg ($2.721 \times 10^{-4}$ mol) of Boc-Gly-OSu. The reaction mixture was stirred at room temperature overnight (22.5 hr). Then the reaction mixture was diluted with 30 mL of $CH_2Cl_2$, washed with water ($2 \times 20$ mL), washed with saturated NaCl (20 mL), dried with $MgSO_4$, and evaporated. Column chromatography on silica gel with $CHCl_3$/MeOH=95:5 afforded 124.9 mg (95%) of Bis-(Boc-Gly)-ODAP as an oil: $R_f$=0.17 ($CHCl_3$/MeOH=95:5), 0.51 ($CHCl_3$/MeOH=90:10) ($I_2$ or $KMnO_4$); MS (ESI) m/z 1015.9 ($M^+$).

To a solution of 123 mg ($1.211 \times 10^{-4}$ mol) of Bis-(Boc-Gly)-ODAP in 3 mL of MeOH was added 3 mL of 1N HCl. Added 2 mL of MeOH and 2 mL of THF to dissolve material that precipitated on addition of the HCl. After 2 hr stirring at room temperature, the reaction was checked by TLC. TLC indicated little deprotection. The reaction mixture was refluxed. After 2 hr, TLC indicated complete deprotection. After 3 hr of reflux, the reaction mixture was rotovapped to remove organic solvents and then lyophilized. The crude HCl salt (off-white solid) was purified by column chromatography on silica gel with $CHCl_3$/MeOH/$NH_4OH$=85:15:1 to afford 77.1 mg (78%) of Bis-Glycine-ODAP as a colorless oil: $R_f$=0.14 ($CHCl_3$/MeOH/$NH_4OH$=85:15:1), 0.40 ($CHCl_3$/MeOH/$NH_4OH$=85:15:2) (ninhydrin, $I_2$ or $KMnO_4$); $^1$H NMR (400 MHz, $CDCl_3$, TMS) 5.4-5.3 (m, 4H), 3.48 (s, 2H), 3.43 (s, 2H), 3.4-3.3 (m, 4H), 3.3-3.2 (m, 2H), 3.2-3.1 (m, 2H), 2.6-2.4 (m, 8H), 2.4-2.3 (m, 4H), 2.1-2.0 (m, 8H), 1.8-1.6 (m, 4H), 1.6-1.5 (m, 4H), 1.4-1.2 (m, 44H), 0.88 (t, J=6.8 Hz, 6H); MS (ESI) m/z 815.9 ($M^+$), 408.5 ($M^{2+}$), 272.7 ($M^{3+}$).

Example 7

Bis-Pyridyl-ODAP

To a suspension of 43.7 mg ($3.550 \times 10^{-4}$ mol) of nicotinic acid in 2 mL of $CHCl_3$ was added 247 L (1.418 mmol) of DIEA. Then 134.4 mg ($3.544 \times 10^{-4}$ mol) of HBTU were added. After stirring for 15 min, a solution of 99.5 mg ($1.419 \times 10^{-4}$ mol) of ODAP in 1 mL of $CHCl_3$ was added to the reaction mixture. After refluxing for 6 hr, the reaction mixture was rotovapped. Then evaporated two times with 5 mL of methanol. The residue was dissolved in $CH_2Cl_2$ (50 mL), washed with saturated $Na_2CO_3$ ($2 \times 25$ mL), dried with $MgSO_4$, and evaporated. Column chromatography on silica gel with $CH_2Cl_2$/MeOH/$NH_4OH$=95:5:0.5 afforded 117.2 mg (91%) of bis-pyridyl-ODAP as an orange oil: $R_f$=0.16 ($CH_2Cl_2$/MeOH/$NH_4OH$=95:5:0.5), 0.45 ($CH_2Cl_2$/MeOH/$NH_4OH$=90:10:1) (UV, $I_2$ or $KMnO_4$); $^1$H NMR (400 MHz, $CDCl_3$, TMS) 8.65 (dd, J=4.8, 1.6 Hz, 2H), 8.62 (br s, 2H), 7.70 (br d, J=8 Hz, 2H), 7.34 (ddd, J=8.0, 4.8, 0.8 Hz, 2H), 5.4-5.3 (m, 4H), 3.6-3.4 (m, 4H), 3.3-3.2 (m, 4H), 2.6-2.3 (m, 8H), 2.2-2.1 (m, 4H), 2.1-2.0 (m, 8H), 1.9-1.8+1.7-1.5 (m, 8H), 1.4-1.1 (m, 44H), 0.88 (t, J=6.8 Hz, 6H); MS (ESI) m/z 911.9 ($M^+$), 456.5 ($M^{2+}$).

Example 8

General Experimental

All suspension cultures were maintained in an appropriate serum-free complete growth media. All cultures were maintained in a humidified atmosphere containing 5-8% CO2 at 37° C. Suspension cultures were seeded at a density of 500,000 cells/mL at the time of transfection in 24 well deep well shake block (2 mL/well). Cells were shaken at 120 rpm (using a 2 cm orbital throw shaker).

The transfection complexes, which are generally ternary complexes, are prepared by mixing the plasmid DNA (pDNA) with an effective amount of an amphipathic compound and an effective amount of a polycation. In some cases, the pDNA is mixed first with serum-free media or other non-toxic solution and then the polycation and amphipathic compound are added sequentially to the mixture. In other cases, the polycation and amphipathic compound are first mixed together prior to adding to the pDNA/serum free media mixture. The mixture containing the ternary complex of pDNA, polycation and amphipathic compound is incubated at room temperature for 15-30 minutes and then added to the cells.

Example 9

Transfection Efficiency of ePEI and Bis-Me-Im-ODAP Relative to Commercially Available Reagents Transfections were performed in duplicate in 24 well deep well shake blocks using suspension CHO cells grown in BD Select CD 1000 medium (CHO-1000). Cells were seeded at 500,000 cells/mL (2 mL per well) at the time of transfection. Transfection competent complexes were prepared by first mixing 2 ug (per well) plasmid DNA (pCIluc luciferase expression plasmid) with 200 ul Opti-PRO SFM media, followed by sequential addition of the polycation and amphipathic compound. Ternary complexes were incubated for 20 minutes before dropwise addition to cultured cells. Cultured cells were grown in 2 mL of appropriate serum-free complete media. No media change is required post-transfection.

Figure 5:
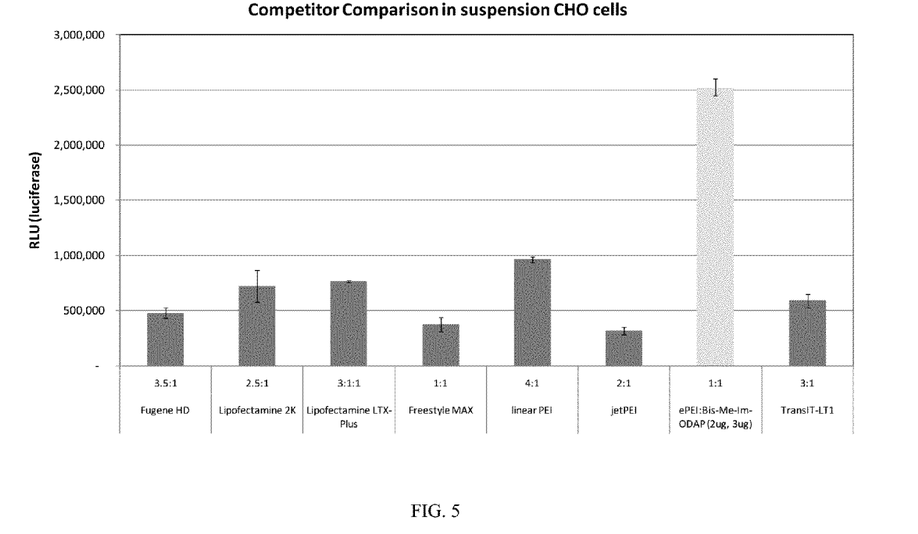
FIG. 5 shows a bar graph comparing transfection efficiency of EPEI and Bis-Me-Im-ODAP relative to commercially available reagents.

In this example EPEI served as the polycation and Bis-Me-Im-ODAP served as the amphipathic compound. The amount of polycation and amphipathic compound (in ug per transfected well) is indicated in parentheses for each condition (FIG. 5). Comparisons were made with several commercially available reagents using optimized ratios of reagent to DNA (noted beneath each bar along x-axis) and following the manufacturer's recommended protocol. Commercially available reagents included Fugene HD (Roche), Lipofectamine 2000 (Life Technologies), Lipofectamine LTX Plus (Life Technologies), FreeStyle MAX (Life Technologies), 25 kDa Linear PEI (Polysciences), JetPEI (PolyPlus), and TransIT-LT1 (MirusBio). Cells were harvested at 24 hours and assayed for luciferase activity using a conventional assay. FIG. 5 depicts the mean (of duplicate samples) in relative light units (RLU) for each experimental condition.

At optimal dose and ratio, EPEI+Bis-Me-Im-ODAP resulted in as much as a 2.5-fold increase in relative light units versus commercially available reagents. This demonstrates the exceptional transfection efficiency given by EPEI+Bis-Me-Im-ODAP when complexed with pDNA and transfected into cells in culture.

Example 10

Testing EPEI with Different Amphipathic Compounds

Transfections were performed in duplicate in 24 well deep well shake blocks using suspension CHO cells grown in BD Select CD 1000 medium (CHO-1000). Cells were seeded at 500,000 cells/mL (2 mL per well) at the time of transfection. Transfection competent complexes were prepared by first mixing 2 ug (per well) plasmid DNA (pCIluc luciferase expression plasmid) with 200 ul Opti-PRO SFM media, followed by sequential addition of the polycation and amphipathic compound. Ternary complexes were incubated for 20 minutes before drop-wise addition to cultured cells. Cultured cells were grown in 2 mL of appropriate serum-free complete media. No media change is required post-transfection.

Figure 6:
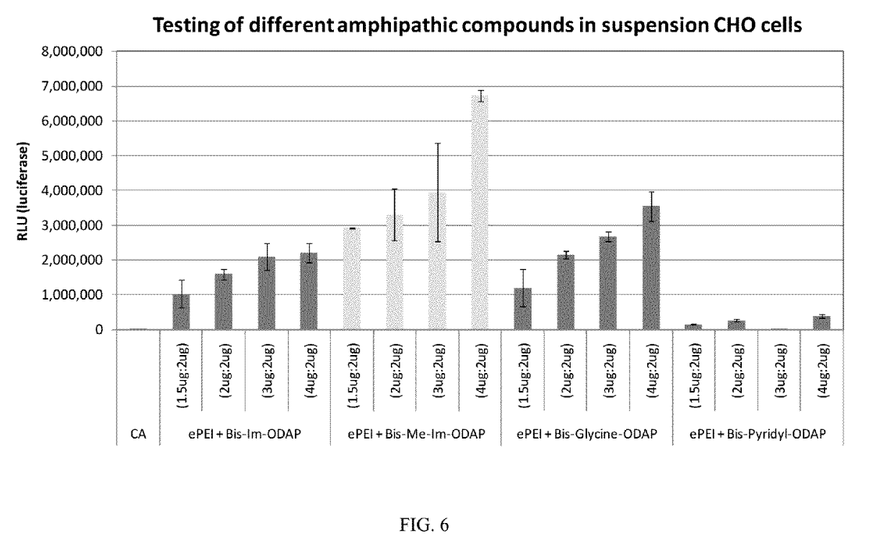
FIG. 6 shows a bar graph testing EPEI with different amphipathic compounds.

In this example EPEI served as the polycation and various lipids including: Bis-Im-ODAP, Bis-Me-Im-ODAP, Bis-Glycine-ODAP or Bis-Pyridyl-ODAP served as the amphipathic compound. The amount of polycation and/or amphipathic compound (in ug per transfected well) is indicated in parentheses for each condition (FIG. 6). Cells were harvested at 24 hours and assayed for luciferase activity using a conventional assay. FIG. 6 depicts the mean (of duplicate samples) in relative light units (RLU) for each experimental condition.

At optimal dose and ratio, EPEI+Bis-Me-Im-ODAP resulted in a 2-25 fold increase in relative light units compared to EPEI other compounds tested (Bis-Im-ODAP, Bis-Glycine-ODAP, and Pyridyl-ODAP). This demonstrates the significant impact that modifications to the amphipathic compound have on transfection efficiency.

Example 11

Testing Bis-Me-Im-ODAP with Different Polycations

Transfections were performed in duplicate in 24 well deep well shake blocks using suspension CHO cells grown in BD Select CD 1000 medium (CHO-1000). Cells were seeded at 500,000 cells/mL (2 mL per well) at the time of transfection. Transfection competent complexes were prepared by first mixing 2 ug (per well) plasmid DNA (pCIluc luciferase expression plasmid) with 200 ul Opti-PRO SFM media, followed by sequential addition of the polycation and amphipathic compound. Ternary complexes were incubated for 20 minutes before drop-wise addition to cultured cells. Cultured cells were grown in 2 mL of appropriate serum-free complete media. No media change is required post-transfection.

Figure 7:
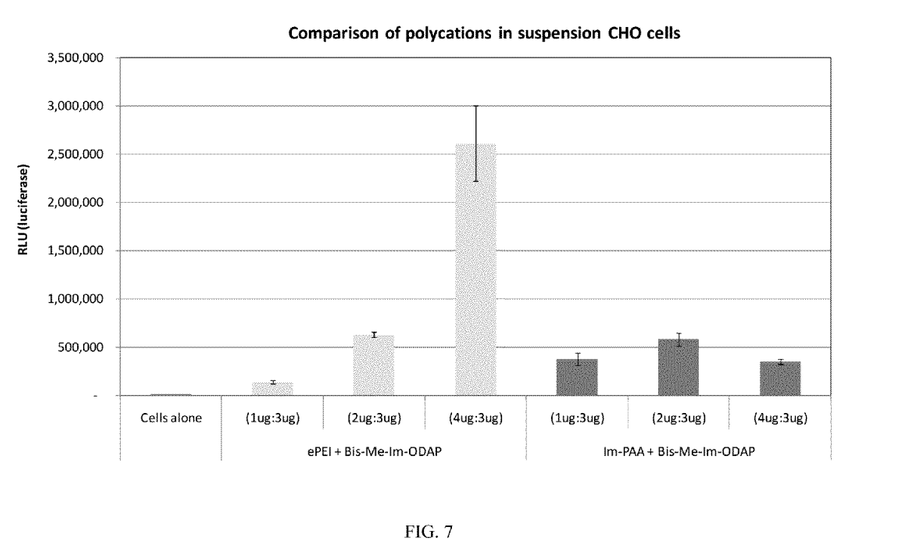
FIG. 7 shows a bar graph testing Bis-Me-Im-ODAP with different polycations.

In this example EPEI or Im-PAA served as the polycation and Bis-Me-Im-ODAP served as the amphipathic compound. The amount of polycation and/or amphipathic compound (in ug per transfected well) is indicated in parentheses for each condition (FIG. 7). Cells were harvested at 24 hours and assayed for luciferase activity using a conventional assay. FIG. 7 depicts the mean (of duplicate samples) in relative light units (RLU) for each experimental condition.

At optimal dose and ratio, EPEI+Bis-Me-Im-ODAP resulted in a nearly 5-fold increase in relative light units compared to ImPAA+Bis-Me-Im-ODAP. This demonstrates the significant impact that polycation choice has on transfection efficiency.

Example 12

EPEI Requires an Amphipathic Compound for Efficient Cellular Transfection

Transfections were performed in duplicate in 24 well deep well shake blocks using suspension CHO cells grown in BD Select CD 1000 medium (CHO-1000). Cells were seeded at 500,000 cells/mL (2 mL per well) at the time of transfection. Transfection competent complexes were prepared by first mixing 2 ug (per well) plasmid DNA (pCIluc luciferase expression plasmid) with 200 ul Opti-PRO SFM media, followed by sequential addition of the polycation and amphipathic compound. In the case of binary complexes (ePEI and pDNA or lipid and pDNA), complexes were formed in the same way with no addition of the corresponding polycation or amphipathic compound. Both ternary and binary complexes were incubated for 20 minutes before drop-wise addition to cultured cells. Cultured cells were grown in 2 mL of appropriate serum-free complete media. No media change is required post-transfection.

Figure 8:
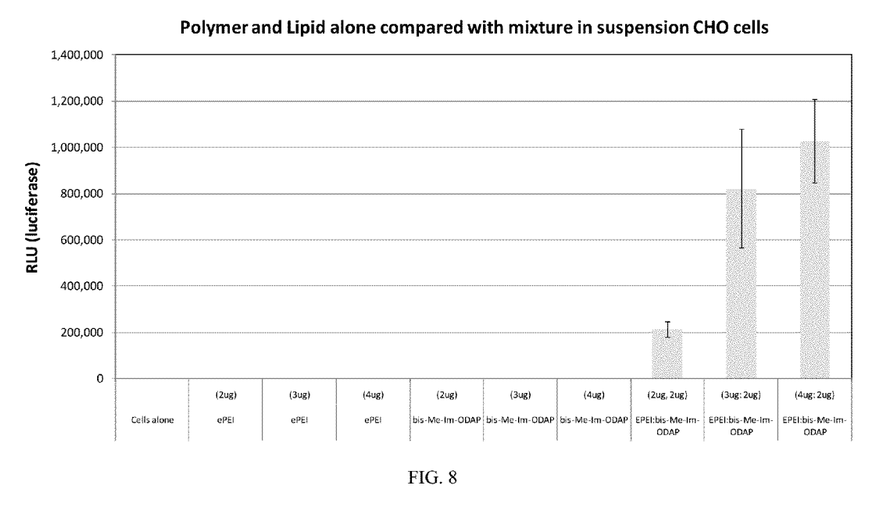
FIG. 8 shows a bar graph indicating that EPEI requires an amphipathic compound for efficient cellular transfection.

In this example EPEI served as the polycation and Bis-Me-Im-ODAP served as the amphipathic compound. The amount of polycation and/or amphipathic compound (in ug per transfected well) is indicated in parentheses for each condition (FIG. 8). Cells were harvested at 24 hours and assayed for luciferase activity using a conventional assay. FIG. 8 depicts the mean (of duplicate samples) in relative light units (RLU) for each experimental condition.

We observed an up to 10,000-fold increase in relative light units when comparing ePEI+Bis-Me-Im-ODAP to ePEI or Bis-Me-Im-ODAP alone. This demonstrates the importance of ternary complexes (as opposed to binary complexes of EPEI and pDNA).

The foregoing is considered as illustrative only of the principles of the invention. Furthermore, since numerous modifications and changes will readily occur to those skilled in the art, it is not desired to limit the invention to the exact construction and operation shown and described. Therefore, all suitable modifications and equivalents fall within the scope of the invention.

We claim:

1. A transfection composition comprising: an amphipathic compound containing an imidazole and a cationic polymer, wherein the amphipathic compound has the structure comprising:

Wherein R1, R2, R3 and R4 are independently selected from the group consisting of alkene and substituent comprising imidazole, wherein at least one of R1, R2, R3 and R4 is a substituent comprising imidazole.

2. The transfection composition of claim 1 wherein the cationic polymer is an acrylamide.

3. The transfection composition of claim 2 wherein the acrylamide comprises an alkyl side group (two or more carbons) containing one or more primary, secondary, or tertiary amines.

4. The composition of claim 1 wherein R1 comprises an imidazole.

5. The composition of claim 1 wherein R2 comprise an imidazole.

6. The composition of claim 1 wherein the amphipathic compound has the structure comprising: